(12) United States Patent
Feinberg (10) Patent No.: US 9,005,244 B2
(45) Date of Patent: Apr. 14, 2015

(54) TISSUE APPROXIMATION DEVICE

(75) Inventor: Marc E. Feinberg, Ringoes, NJ (US)

(73) Assignee: Ethicon, Inc., Somerville, NJ (US)

( * ) Notice: Subject to any disclaimer, the term of this patent is extended or adjusted under 35 U.S.C. 154(b) by 1428 days.

(21) Appl. No.: 10/674,653

(22) Filed: Sep. 30, 2003

(65) Prior Publication Data

US 2005/0070927 A1   Mar. 31, 2005

(51) Int. Cl.
*A61B 17/08* (2006.01)
*A61B 17/28* (2006.01)
*A61B 17/00* (2006.01)

(52) U.S. Cl.
CPC ........... *A61B 17/2816* (2013.01); *A61B 17/083* (2013.01); *A61B 17/085* (2013.01); *A61B 17/0057* (2013.01)

(58) Field of Classification Search
USPC ......... 606/150, 218, 207, 208, 205, 216, 213, 606/210, 211, 215, 142, 221, 148; 294/99.2
See application file for complete search history.

(56) References Cited

U.S. PATENT DOCUMENTS

| | | | |
|---|---|---|---|
| 889,662 A | 6/1908 | Coulter | |
| 2,003,629 A * | 6/1935 | Coffey | 15/236.05 |
| 3,296,193 A * | 1/1967 | Walsh et al. | 524/134 |
| 3,611,842 A | 10/1971 | Skipper | |
| 3,754,331 A * | 8/1973 | Agnone | 433/160 |
| 3,926,193 A * | 12/1975 | Hasson | 606/218 |
| 3,933,158 A | 1/1976 | Haverstock | |
| 3,971,384 A | 7/1976 | Hasson | |
| 4,114,624 A | 9/1978 | Haverstock | |
| 4,212,305 A | 7/1980 | Lahay | |
| 4,724,838 A * | 2/1988 | Hasson | 606/148 |
| 4,732,146 A | 3/1988 | Fasline | |
| 4,821,719 A * | 4/1989 | Fogarty | 606/158 |
| 4,825,866 A | 5/1989 | Pierce | |
| 5,156,431 A | 10/1992 | Lowe | |
| 5,259,835 A | 11/1993 | Clark et al. | |
| 5,300,065 A | 4/1994 | Anderson | |
| 5,514,148 A | 5/1996 | Smith | |
| 5,562,705 A | 10/1996 | Whiteford | |
| 5,611,794 A | 3/1997 | Sauer et al. | |
| 5,752,973 A | 5/1998 | Kieturakis | |
| 5,891,017 A * | 4/1999 | Swindle et al. | 600/205 |
| 5,893,879 A | 4/1999 | Hirshowitz et al. | |
| 5,972,021 A | 10/1999 | Huttner et al. | |
| 6,042,599 A * | 3/2000 | Huttner et al. | 606/205 |
| 6,050,266 A * | 4/2000 | Benetti et al. | 128/898 |
| 6,120,525 A | 9/2000 | Westcott | |
| 6,394,951 B1 * | 5/2002 | Taylor et al. | 600/210 |
| 6,494,896 B1 | 12/2002 | D'Alessio et al. | |
| 2002/0065534 A1 | 5/2002 | Hermann et al. | |

* cited by examiner

*Primary Examiner* — Elizabeth Houston
*Assistant Examiner* — Jing Ou
(74) *Attorney, Agent, or Firm* — Roberts Mlotkowski Safran & Cole, P.C.

(57) ABSTRACT

A tissue approximation device comprising two elongate arms, an attachment means to secure the elongate arms to each other, adhesive pads on at least a portion of the elongate arms to anchor the tissue approximation device to the skin, and a locking means to lock the elongate arms in place relative to each other.

11 Claims, 12 Drawing Sheets

TISSUE APPROXIMATION DEVICE

BACKGROUND OF THE INVENTION

The present invention is directed to a tissue approximation device that is capable of maintaining approximation of a wound without substantial eversion of the edge surfaces of the wound and without requiring the physician or health care attendant to manually secure the device.

Prior art tissue approximation devices have been described. For example, U.S. Pat. No. 6,042,599 discloses a tissue approximation forceps that is particularly useful in approximating edge surfaces of a wound where liquid topical adhesive is to be used. The forceps described in this reference comprise two leg members having grip members with grip surfaces that lie in a common plane. The grip surfaces are described as a plurality of parallel longitudinally extending, generally, V-shapes projections or sharp projections. This reference discloses that when the handle of the forceps is squeezed together, the grip members move towards one another in the same plane, in a direction generally parallel to the skin tissue, while the grip surfaces engage the skin tissue on opposite sides of the wound, such that the opposite edges of the wound are moved together without everting the edge surfaces. Specifically, the projections on the grip surfaces are urged into and against the skin tissue to approximate the wound and frictionally hold the engaged skin tissue. The reference also discloses a ratchet type-locking arm on the handle that fits the other handle member when the forceps are in the closed position. However, a problem associated with this tissue approximation forceps is that the physician must apply a force perpendicular to the skin tissue to maintain contact between the gripping surfaces and the skin tissue, in order to maintain approximation of the wound. Therefore, this device will not free-up the physician's hand.

Accordingly, it is desirable to have a tissue approximation device that is capable of maintaining approximation of a wound without substantial eversion of the edge surfaces of the wound during application and curing of a topical skin closure adhesive on a wound, without requiring the physician or health care attendant to manually secure the device.

BRIEF SUMMARY OF THE INVENTION

Described herein is a tissue approximation device that is capable of maintaining approximation of a wound without substantial eversion of the edge surfaces of the wound during application of a topical skin adhesive, an adhesive film or skin staples to close a wound, without requiring the physician or health care attendant to manually secure the approximation device. In particular, described herein is a tissue approximation device comprising two elongate arms, an attachment means to secure the two elongate arms to each other, adhesive pads to anchor the tissue approximation device to the skin, and a locking means to lock the two elongate arms in place relative to each other In one embodiment, the elongate arms may each have a handle and a tong, such as in a pair of parallel forceps. An adhesive pad is on the distal end of each of the tongs, which may be located on the distal ends of the elongate arms of the parallel forceps. Further, the attachment means may be a pair of slidable bosses, while the locking means may be a ratchet mechanism on the forceps.

In another embodiment, an adhesive pad is on the distal end of each of the tongs, which are located on the distal ends of a pair of forceps. Further, the attachment means may be a yoke on the forceps, while the locking means may be a ratchet mechanism on the forceps.

The adhesive pads in either of these embodiments may be of several forms. For example, the adhesive pad may be fixedly attached to the distal end of each of the tongs. The adhesive pad may have a first adhering surface and a second surface having a socket mechanism that communicates with a ball on the distal end of each of the tongs, and the adhesive pad is optionally rotatable around the ball. Alternatively, the second surface of the adhesive pad may have a ball and the distal end of each of the tongs may have a socket mechanism. Alternatively, the adhesive pads may have a first adhering surface and a second surface having female receiving mechanism that communicates with a male protrusion on the distal end of each of the tongs; or the adhesive pad may have a first adhering surface and a second surface having a male protruding mechanism that communicates with a female receiving mechanism on the distal end of each of the tongs.

DETAILED DESCRIPTION OF THE INVENTION

The tissue approximation device of the present invention approximates a wound without substantially everting the edge surfaces of the wound during application of a topical skin adhesive, an adhesive film or skin staples to close a wound.

Figure 1:
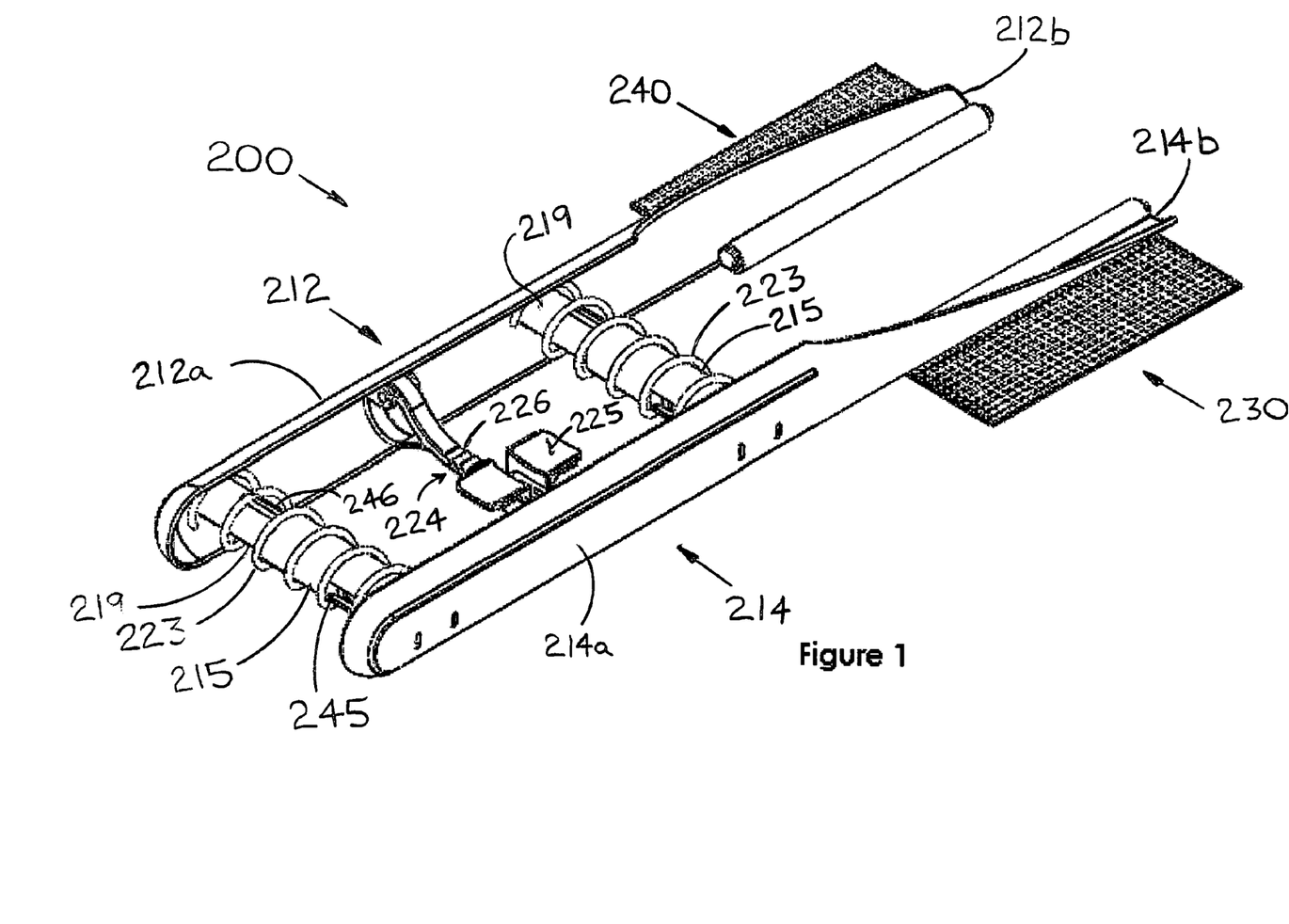
FIG. 1 is representative of one embodiment of the present invention, where the adhesive pad is on the distal end of each of the tongs, which are located on the distal ends of a pair of parallel forceps.
Figure 6:
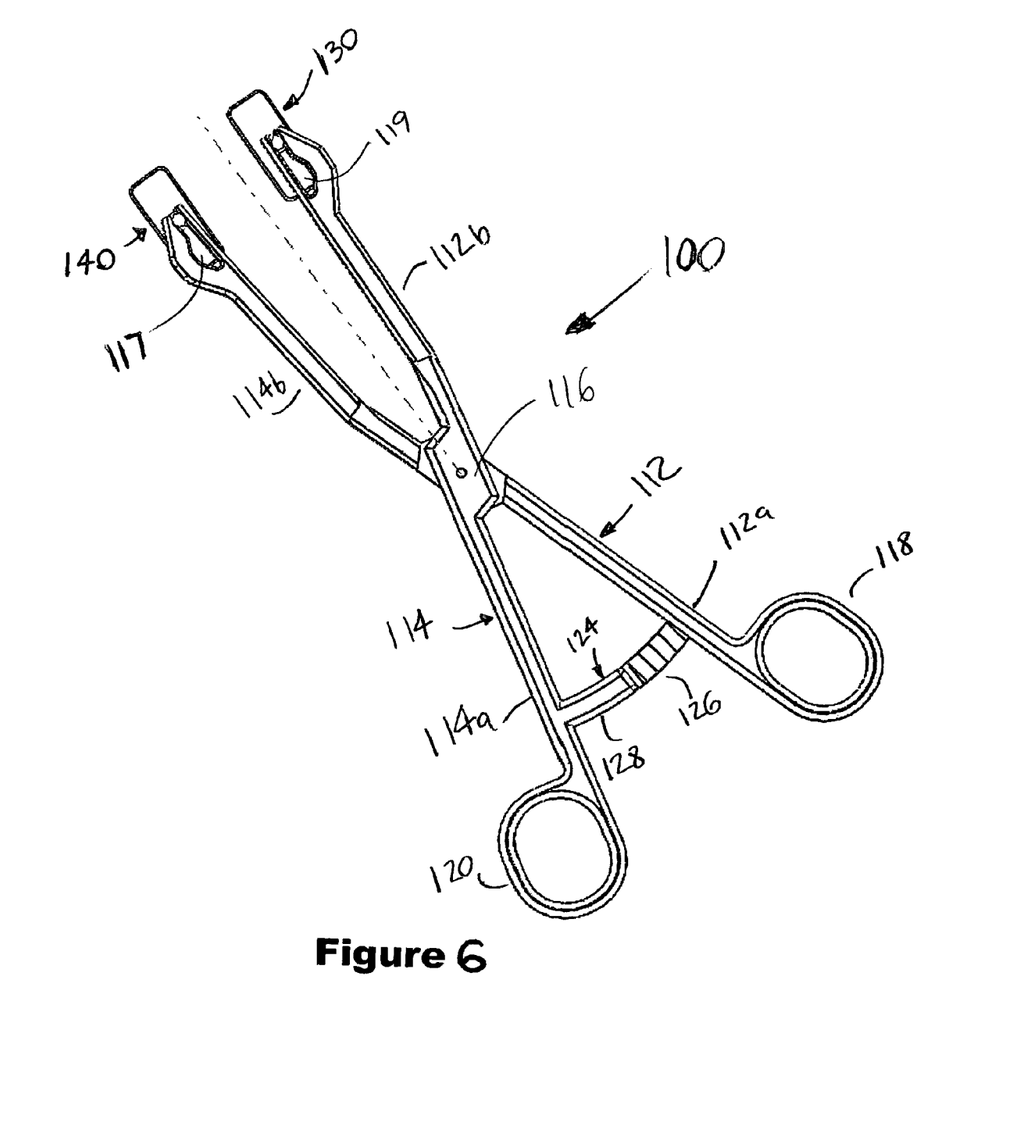
FIG. 6 is representative of a forceps embodiment of the approximation device, where the adhesive pad is on the distal end of each of the tongs.

The tissue approximation device may be made of any shape to accommodate the adhesive pad described below. In general, the device may have a pair of elongate arms that are interconnected and substantially similar to each other, each may have a handle and a tong, the tong portion being located on the distal end of the elongate arm. The attachment means of the tissue approximation device hold the pair of elongate arms in a position relative to each other. As an example, the tissue approximation device may be either the parallel forceps as shown in FIG. 1 or the forceps as shown in FIG. 6. Such forceps may be constructed of any material including metal or plastic compositions.

Figure 7:
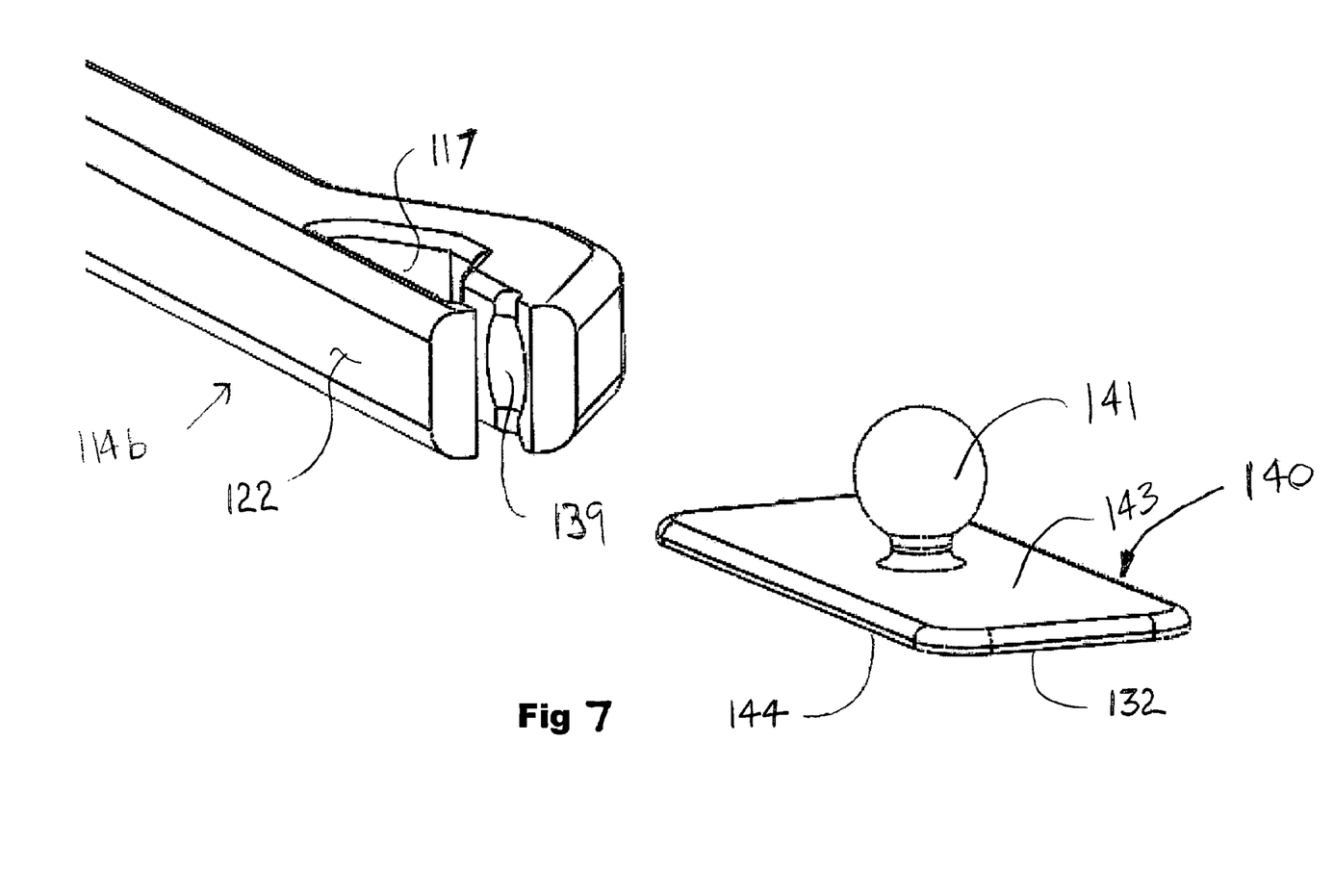
FIGS. 7 and 8 depict various embodiments of the adhesive pads.
Figure 8:
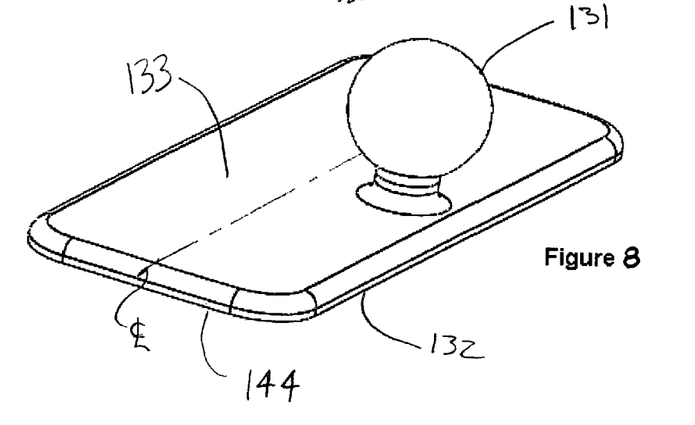
Figure 9:
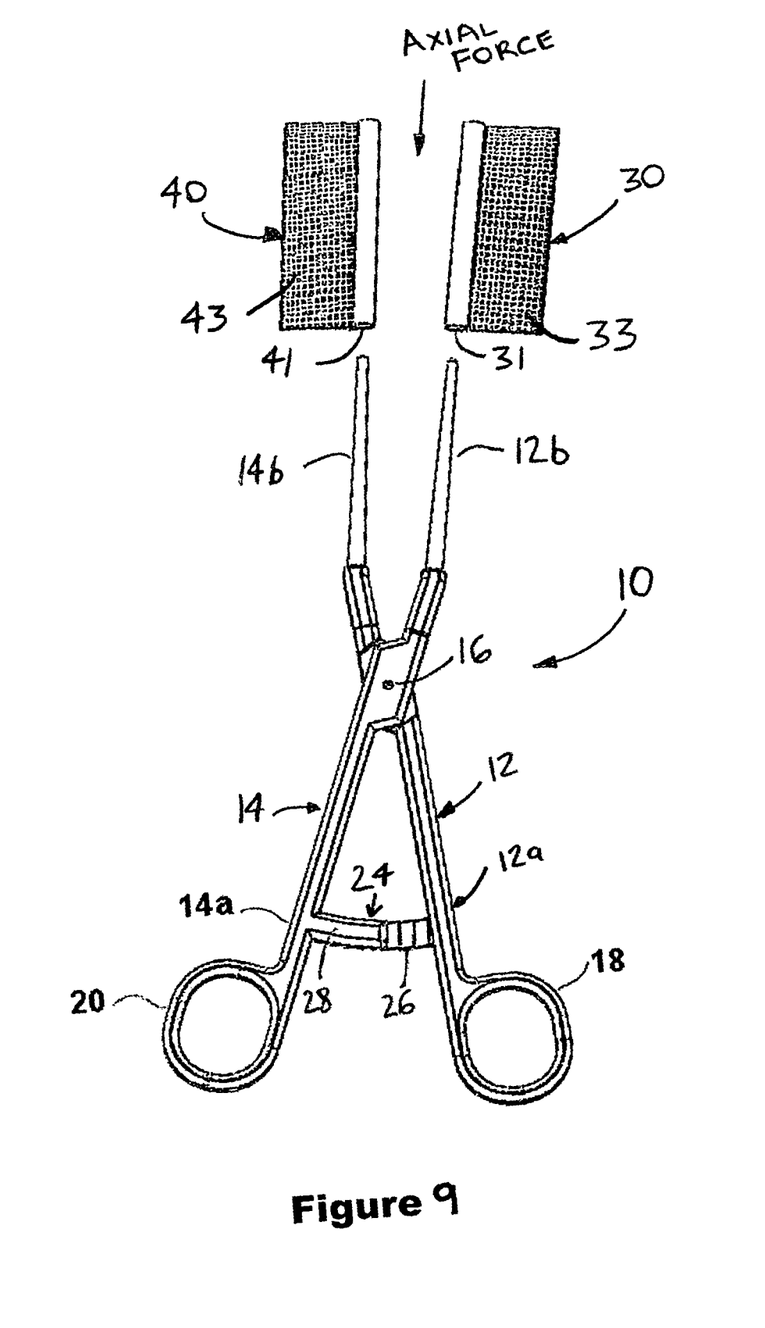
FIG. 9 is an exploded view of the adhesive pad.

As discussed above, the tissue approximation device may be a pair of forceps where the tongs accommodate the adhesive pad. The adhesive pad may be pre-assembled, or may be fixedly attached to or detachable from the distal end of each of the tongs. The adhesive pads may have a first adhering surface and a second surface having a socket mechanism that communicates with a ball on the distal end of each of the tongs, and the adhesive pad is optionally rotatable around the ball (FIG. 12); or the second surface of the adhesive pad may have a ball that communicates with a socket assembly on the distal end of each of the tongs as shown in FIGS. 7 and 8. Alternatively, the adhesive pad may have a first adhering surface and a second surface having a female receiving mechanism that communicates with a male protrusion on the distal end of each of the tongs; or the adhesive pad may have a first adhering surface and a second surface having a male protruding mechanism that communicates with a female receiving mechanism on the distal end of each of the tongs. The adhesive pads may be made to have a surface having a ball/socket mechanism or a female/male mechanisms by injection molding, stamping and rolling, or by a combination of extrusion and rolling or other suitable means. For example, a part having a first flat surface and a second surface having the ball or socket mechanism or the female or male mechanism may be made by injection molding plastic; followed by coating the first flat surface of the part with an adhesive material to form the adhesive pad. Alternatively, the adhesive pad may have a first adhering surface and a passageway therein such that a longitudinal edge of the distal end or the distal end itself of each of the tongs communicates with said passageway as shown in FIGS. 1 and 9. The adhesive pads may be made to have such a passageway by injection molding or extruding plastic into a part having a first surface, a second surface and the passageway; followed by coating the first surface of the part with an adhesive material to form the adhesive pad. If the approximation device is intended to be used during application of a topical skin adhesive, the adhesive pads may be made from any material that has relatively low bondability to the skin adhesive, including but not limited to polyolefins.

The adhesive pads are specifically designed such that the adhering surface has high shear resistance to hold the skin tissue adjacent to the approximating wound and low peel resistance for easy removal from the skin tissue after the topical wound adhesive has cured. The adhesive surface may be formed from one or more adhesive materials selected from the group consisting of polymeric acrylics, polyisobutylene, polyurethane, polymeric silicone and copolymers of these materials. The thickness of the adhesive may be about 0.0015 to about 0.005 inches and may be applied directly to the adhesive pad or to both sides of a polyethylene foam substrate having a total thickness of between about 0.025 inches and 0.075 inches, which in turn is attached to the adhesive pad. The preferred adhesive has a peel strength between about 50 and 150 oz/in when tested according to PSTC Method #1 Mod./180°.

Figure 3:
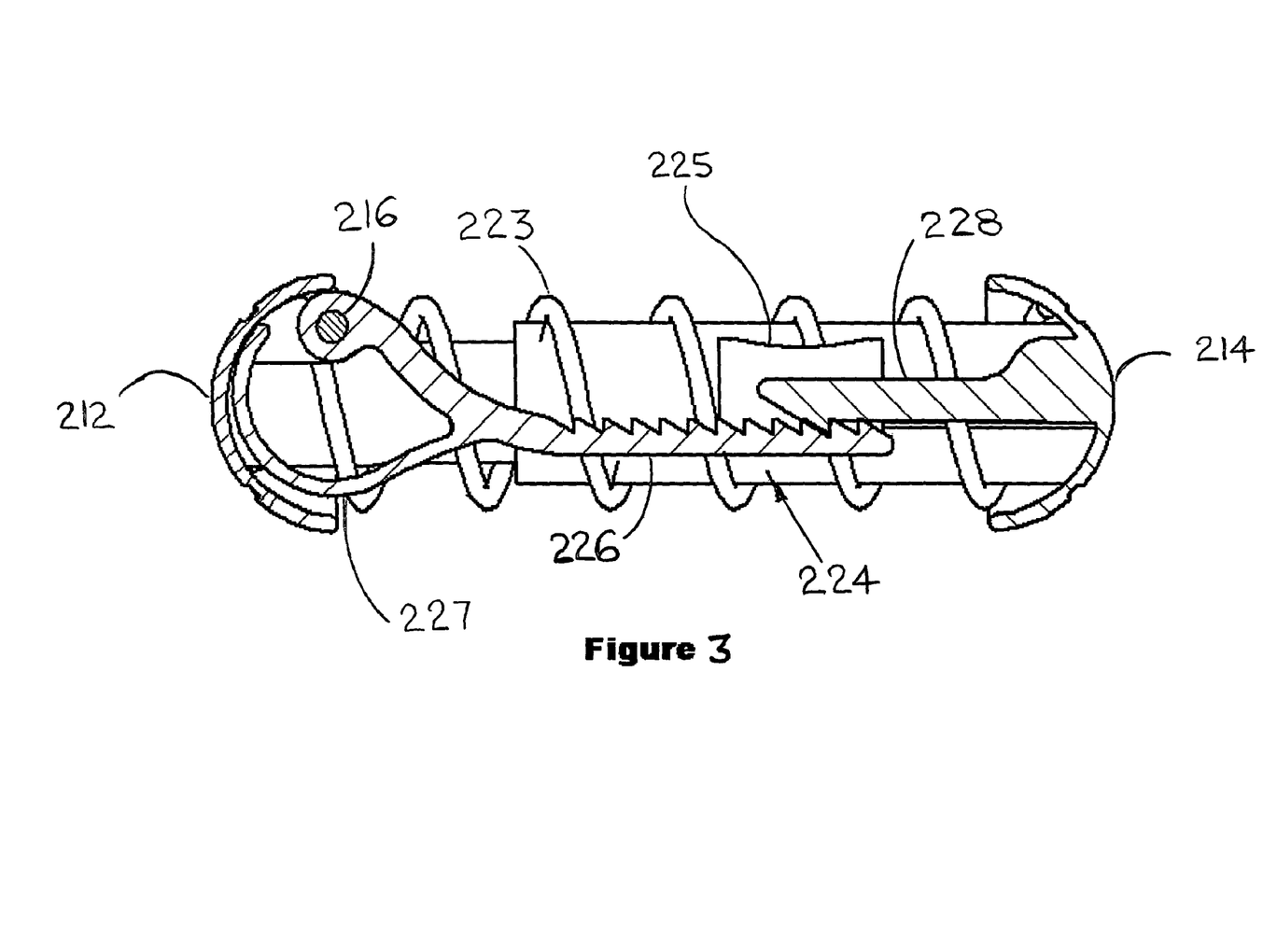
FIG. 3 is a section view through FIG. 1 illustrating a locking means shown in the embodiment of FIG. 1.

Additionally, the tissue approximation device has locking means to lock the two elongate arms described above in a fixed position relative to each other. For example, the locking means may be a ratchet mechanism having a ratchet catch and a ratchet arm with a plurality of ratchet teeth, as shown in FIG. 3. Alternatively, the ratchet catch may be an indentation or cutout on the handle of one elongate arm that fits into ratchet teeth of a ratchet arm attached to the handle of the other elongate arm. Alternatively, ratchet teeth of a ratchet arm attached to the handle of one of the elongate arms may catch the edge of the handle of the other elongate arm, thereby locking the elongate arms in a fixed position relative to each other.

In the embodiment shown in FIG. 1, the tissue approximation device is shown and designated generally by the numeral 200. The approximation device 200 has a rigid elongate arm 212, which is interconnected with and substantially similar to a rigid elongate arm 214. Elongate arms 212 and 214 may be of one-piece construction and each may have a handle 212a and 214a and tong 212b and 214b. Tongs 212b and 214b may removeably hold adhesive pads 230 and 240.

Figure 4:
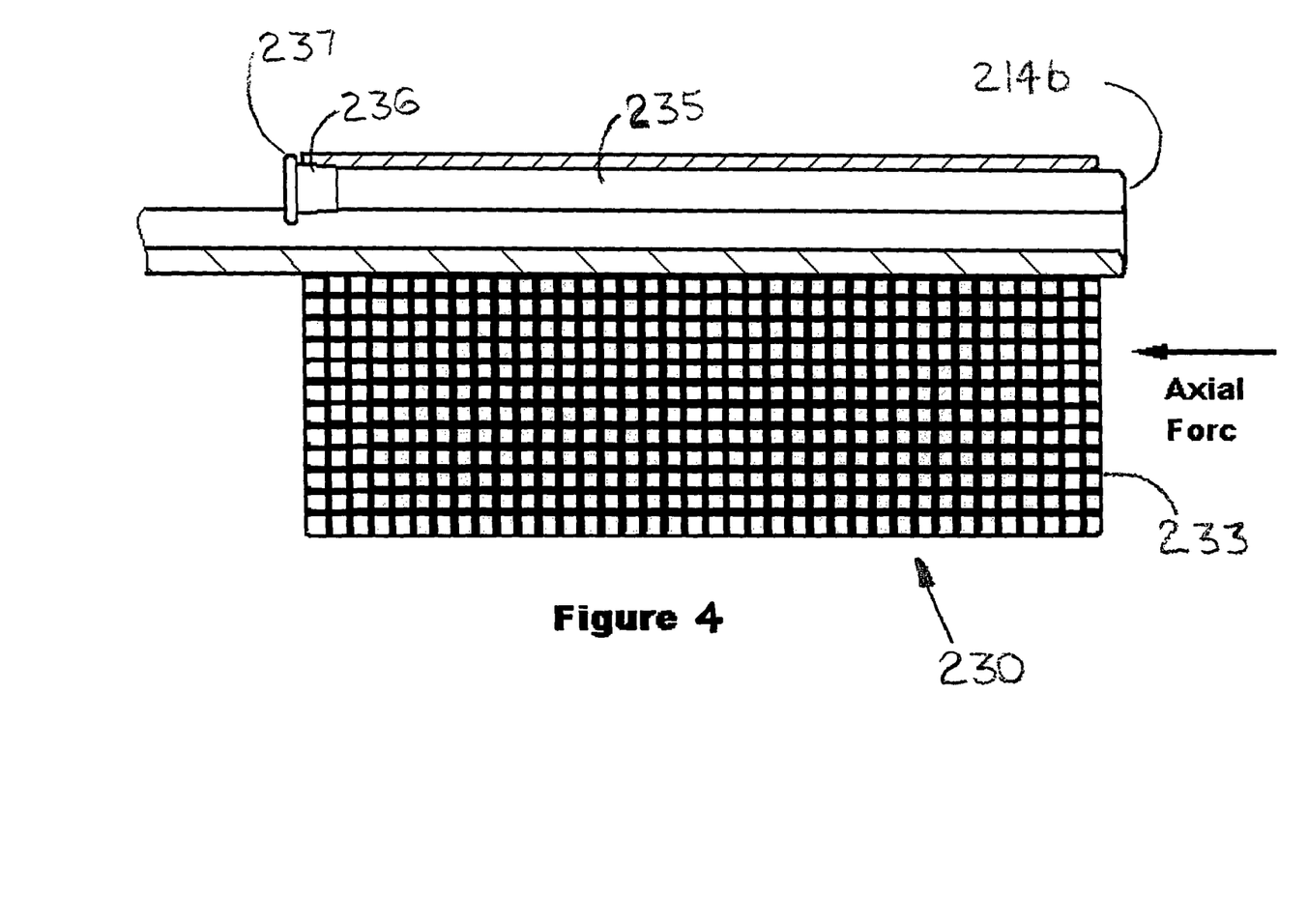
FIG. 4 is a partial section view of the distal end of the tong and the adhesive pads.
Figure 5:
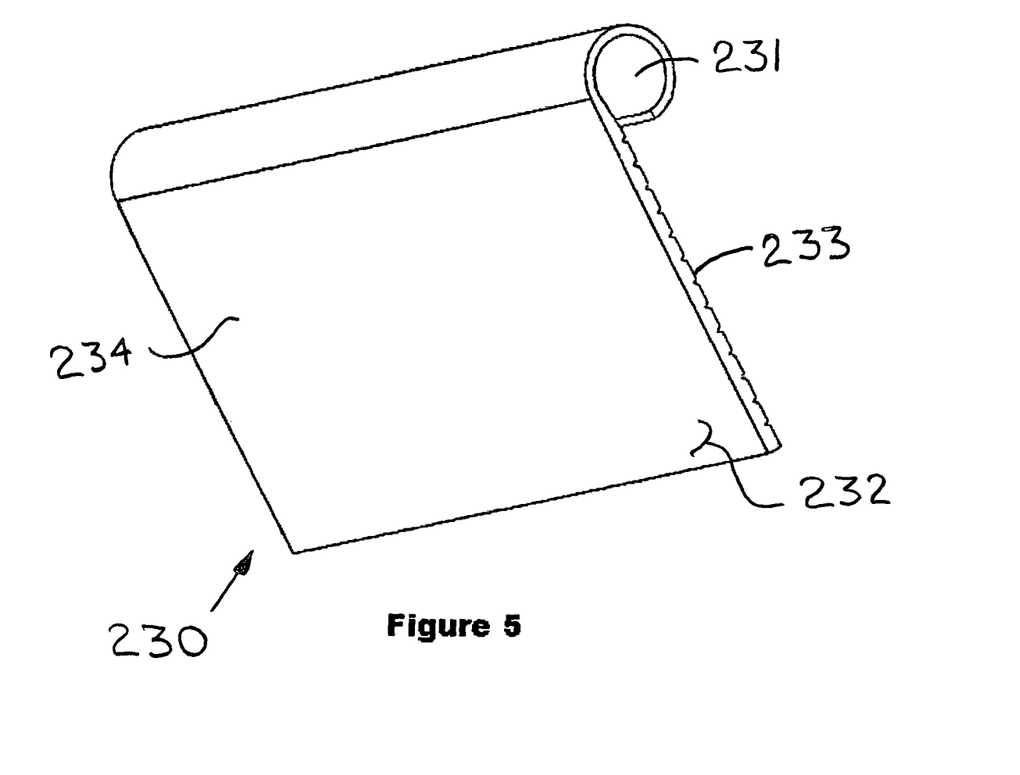
FIG. 5 depicts an embodiment of the adhesive pad.

Referring to FIG. 4 the adhesive pads 230 and 240 may be pre-assembled, or may be fixedly attached to or removable from the distal end of each of the tongs. Tongs 212b and 214b may contain a cylindrical shape 235 and taper portion 236 for receiving and removeably holding adhesive pads 230 and 240. The tongs and adhesive pads interface may be designed to allow the adhesive pads to pivot about the cylindrical shape thus allowing the adhesive pads to conform to various anatomical structures such as a wrist or back. In this embodiment when positioning adhesive pads 230, 240 onto handles 212a, 214a (which are shown in FIG. 1), applying an axial force to adhesive pads 230, 240 towards handles 212a and 214a creates a slight interference fit between the taper 236 outside diameter and inside diameter (through hole 231) of the adhesive pads 230 and 240. This interference fit aids in the alignment of the adhesive pads 230 and 240 with the anatomical structure and prevent the adhesive pads from flopping around during wound application. As shown in FIGS. 4 and 5 adhesive pads 230 and 240 have a through hole 231 that match the cylindrical shape 235. At the proximal end of taper 236 there may be an adhesive pad stop 237, which limits the traverse motion of the adhesive pads during assembly and use. The adhesive pads 230 and 240 have a first adhering surface 232 and a second surface that may have a serrated feature 233 to increase flexibility of the adhesive pads to further conform to various anatomical structures. The adhesive pads 230 and 240 have a release paper 234 that would be stripped off from the adhesive pads to expose the pressure sensitive adhering surface 232.

Figure 2:
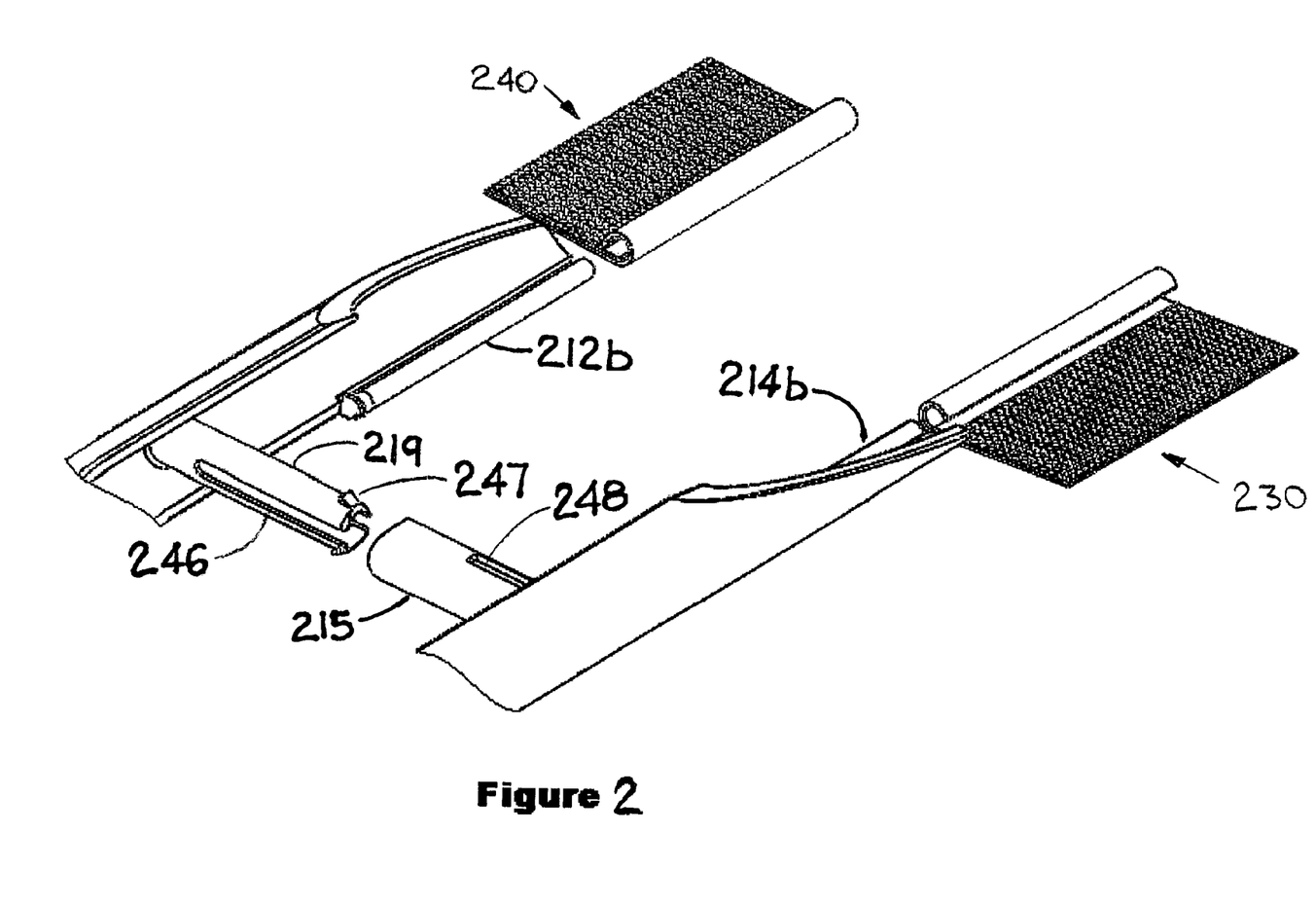
FIG. 2 is an exploded view of an attachment means and the adhesive pads on the embodiment shown in FIG. 1.

Elongate arms 212 and 214 are on the same plane and movably connected to each other for example by bosses 215 and 219 as shown in FIG. 2. The outside diameter of boss 219 is slightly smaller than the inside diameter of boss 215 allowing elongate arms 212, 214 move in a parallel motion. Bosses 215 and 219 may engage in such a way to limit outward travel of elongate arms 212 and 214. For example, boss 219 contains at least one slot 246 that allows at least one ratchet tooth 247 to flex inward upon assembly with boss 215. Boss 215 may contain a receiving slot 248 that connectively receives single ratchet tooth 247 of boss 219. For example, the bosses in this embodiment may be both the attachment means and the locking means.

Ratcheting mechanism 224 shown in FIG. 3 may comprise a flexible ratchet arm 226 pivotally connected at yoke 216 and mounted on first elongate arm 212. Yoke 216 may be made of a stainless steel threaded fastener or pin. Ratcheting mechanism 224 may secondly comprise a ratchet catch 228 rigidly mounted on second elongate arm 214, with ratchet arm 226 and ratchet catch 228 in engaging relationship. More particularly, ratchet arm 226 and ratchet catch 228 engage each other so as to prevent elongate arms 212 and 214 from separating until such time as an operator depresses the ratchet release lever 225 in order to lift ratchet arm 226 away from ratchet catch 228. Ratcheting mechanism 224 prevents first and second tongs 212b, 214b from inadvertently separating from each other. Ratchet arm 226 comprises a plurality of individual ratchet teeth against which ratchet catch 228 engage. As is well known, successive ratchet teeth are separated from each other by a substantially fixed linear distance and ratchet catch 228 can only engage ratchet arm 226 at a number of positions roughly equal to the number of individual ratchet teeth. Ratchet arm 226 may contain an integrally connected leaf spring 227 that applies a load in the counterclockwise direction and whose motion is limited by ratchet catch 228. The load applied by leaf spring 227 in this direction enables the ratchet arm 226 to continuously engage the ratchet catch 228. Ratchet mechanism 224 is designed such that when the ratchet catch 228 is engaged with the first ratchet tooth of ratchet arm 226, the tissue approximation is defined herein as being in a closed position, and tongs 212b and 214b remain parallel to each other and are non-contiguous such that the distance between the distal end of tongs 212b and 214b allows access to the wound for application of a permanent wound closure means.

As shown in FIG. 1, handles 212a and 214a are moved toward each other by compressing compression springs 223 which have a spring rate adequate enough to overcome frictional forces between bosses 215, 219 and secure ratchet arm 226 and ratchet catch 228 in engaging relationship. Compression springs 223 may be located on the outside or inside of bosses 215, 219.

In the embodiment shown in FIG. 6, the tissue approximation device is shown and designated generally by the numeral 100. The approximation forceps 100 have a flexible elongate arm 112, which is interconnected with and substantially similar to a flexible elongate arm 114. Elongate arms 112 and 114 each has a handle 112a and 114a and tong 112b and 114b and may be pivotally connected at attachment means, yoke 116. First and second elongate arms 112, 114 are pivoted in a scissors fashion. Handles 112a and 114a lie on the same plane and have at a proximal end thereof finger grips 118 and 120.

The tongs and adhesive pads interface may be designed to pivot multi-directionally by means of a ball and socket mechanism shown in FIGS. 7 and 8 thus allowing the adhesive pads to conform to various anatomical structures such as a wrist or back. In addition this embodiment provides a means of rotating the adhesive pads with ball and socket 139, 141 to cooperate with yoke 116 allowing adhesive pads 130 and 140 to remain parallel to each other during wound approximation. The multi-directional pivoting motion can be limited by changing the distance from the center point of the ball 131 to surface 133 of adhesive pads 140 or 130 so rotation of the adhesive pads are more parallel to tongs 112b and 114b still allowing adhesive pads 130 and 140 to remain parallel to each other during wound approximation. The ball and socket 139, 141 design includes a slight interference fit allowing the alignment of adhesive pads 130 and 140 with the target anatomical structure and preventing the adhesive pads from flopping around during alignment and application. Preferably, adhesive pads 130, 140 remain parallel to each other and are non-contiguous such that the distance between the adhesive pads 130, 140 allows access to the wound for application of a permanent wound closure means.

Figure 12:
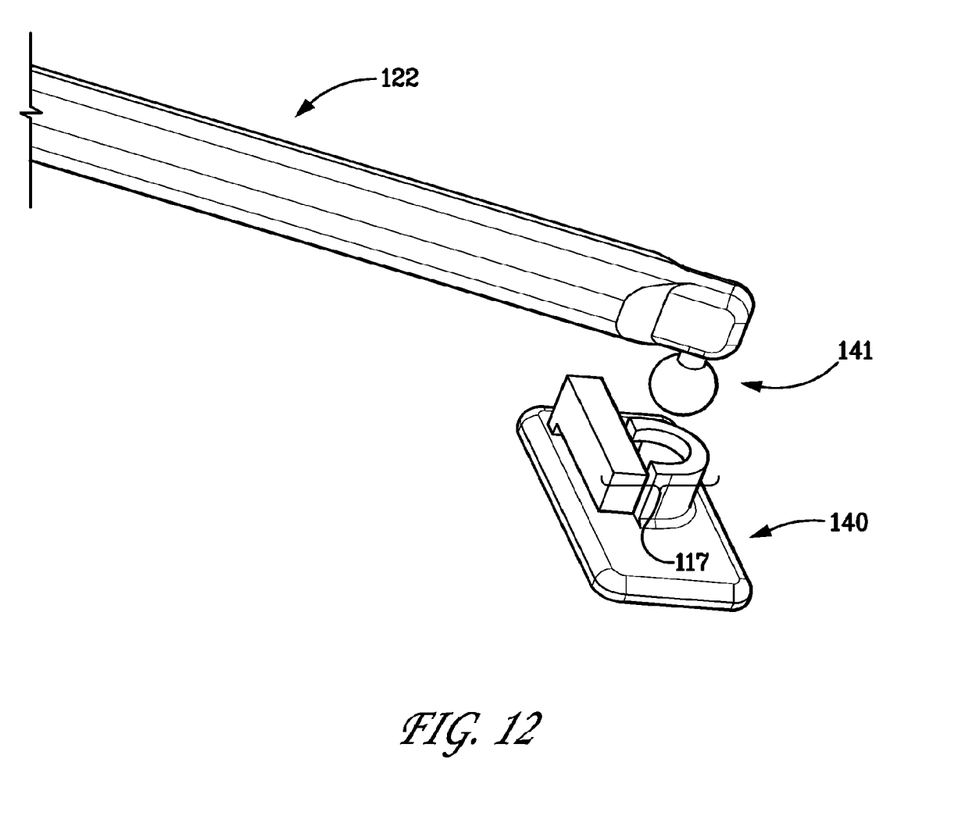
FIG. 12 depicts another embodiment of the adhesive pads.

As shown in FIGS. 7 and 8, tongs 112b and 114b include a recess 117, 119 that allows flex arm 121, 122 to deflect when ball 131, 141 of adhesive pad 130, 140 is installed into socket recess 138, 139. The adhesive pads 130 and 140 have a first adhering surface 132 and a second surface having a release paper 144 that would be stripped off from the adhesive pads to expose the pressure sensitive adhering surface 132. When adhesive pad 140 or 130 the ball 131 are offset from the centerline of surface 133 as shown in FIG. 8, clearance between the tongs is increased and tissue eversion may be controlled during approximation. Alternatively, as shown in FIG. 12, the ball 141 can be disposed on the distal end of flex arm 122, and recess 117 forming the socket recess (not shown) can be disposed on the second surface of the adhesive pads 140.

As shown in FIG. 6, immediately distal of finger grips 118, 120 is a ratcheting mechanism 124. Ratcheting mechanism 124 comprises a ratchet arm 126 mounted on first elongate arm 112 and a ratchet catch 128 mounted on second elongate arm 114, with ratchet arm 126 and ratchet catch 128 in engaging relationship. More particularly, ratchet arm 126 and ratchet catch 128 engage each other so as to prevent finger grips 118, 120 from separating until such time as an operator applies a twisting movement in order to lift ratchet catch 128 away from ratchet arm 126. Ratcheting mechanism 124 prevents first and second tongs 112b, 114b from inadvertently separating from each other. Ratchet arm 126 comprises a plurality of individual ratchet teeth against which ratchet catch 128 engage. As is well known, successive ratchet teeth are separated from each other by a substantially fixed linear distance and ratchet catch 128 can only engage ratchet arm 126 at a number of positions roughly equal to the number of individual ratchet teeth. Ratchet mechanism 124 is designed such that when the first ratchet catch is engaged with ratchet arm 126, the tissue approximation is defined herein as being in a closed position and the distance between the distal end of tongs 112b and 114b allows access to the wound for application of a permanent wound closure means.

The tissue approximation device described in FIG. 6 may be made by injection molding plastic and utilizing a yoke pin of metal that is adequately secured by threads, rivet or bonding. The forceps may also be made of stainless steel, in which case the pivot is fixedly inserted into first arm 112 and through which second arm 114 passing in a manner well known in the art of forceps making.

Figure 10:
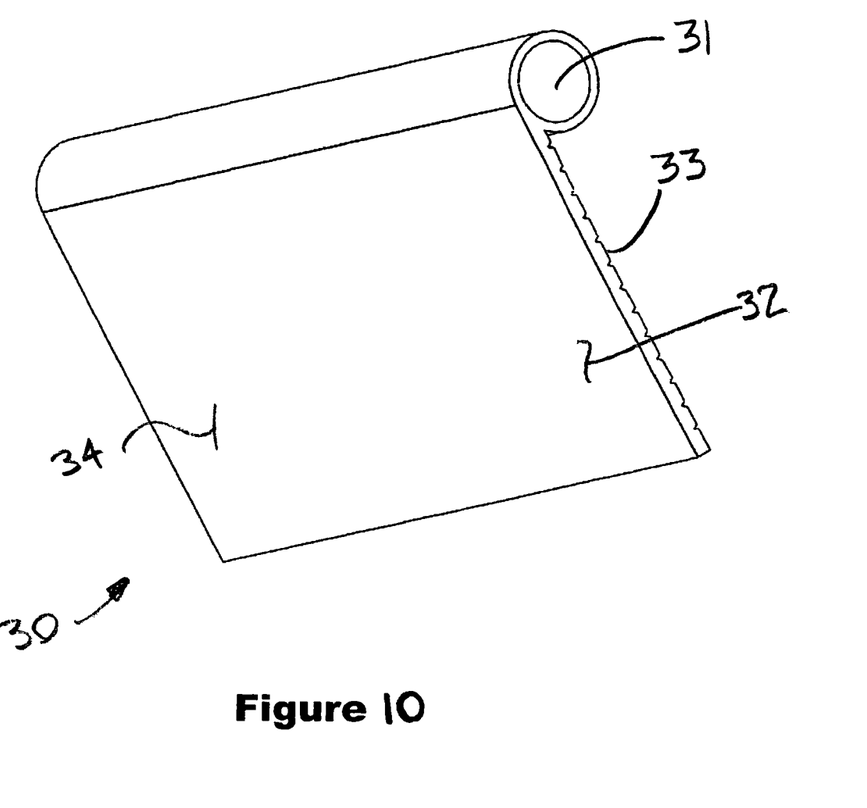
FIG. 10 depicts an embodiment of the adhesive pad.

Referring now to FIG. 9, the tissue approximation device shown and designated generally by the numeral 10 is similar to the device shown and depicted in FIG. 6, except that tongs 12b and 14b have a taper for receiving and removeably holding adhesive pads 30 and 40. Specifically, adhesive pads 30 and 40 have a tapered hole 31 and 41 that match the taper of tongs 12b and 14b. In this embodiment applying an axial force to adhesive pads 30 and 40 toward handles 12a and 14a creates an interference fit between the tongs 12b, 14b outside diameter and inside diameter of the adhesive pads 30 and 40 to aid in the alignment of the adhesive pads 30 and 40 with the anatomical structure and to prevent the adhesive pads from flopping around during wound application. In FIG. 10, adhesive pads 30 and 40 have a first adhering surface 32 and a second surface having a serrated feature 33 to increase flexibility of the adhesive pads to further conform to various anatomical structures. The adhesive pads 30 and 40 have a release paper 34 that would be stripped off from the adhesive pads to expose the pressure sensitive adhering surface 32.

Figure 11:
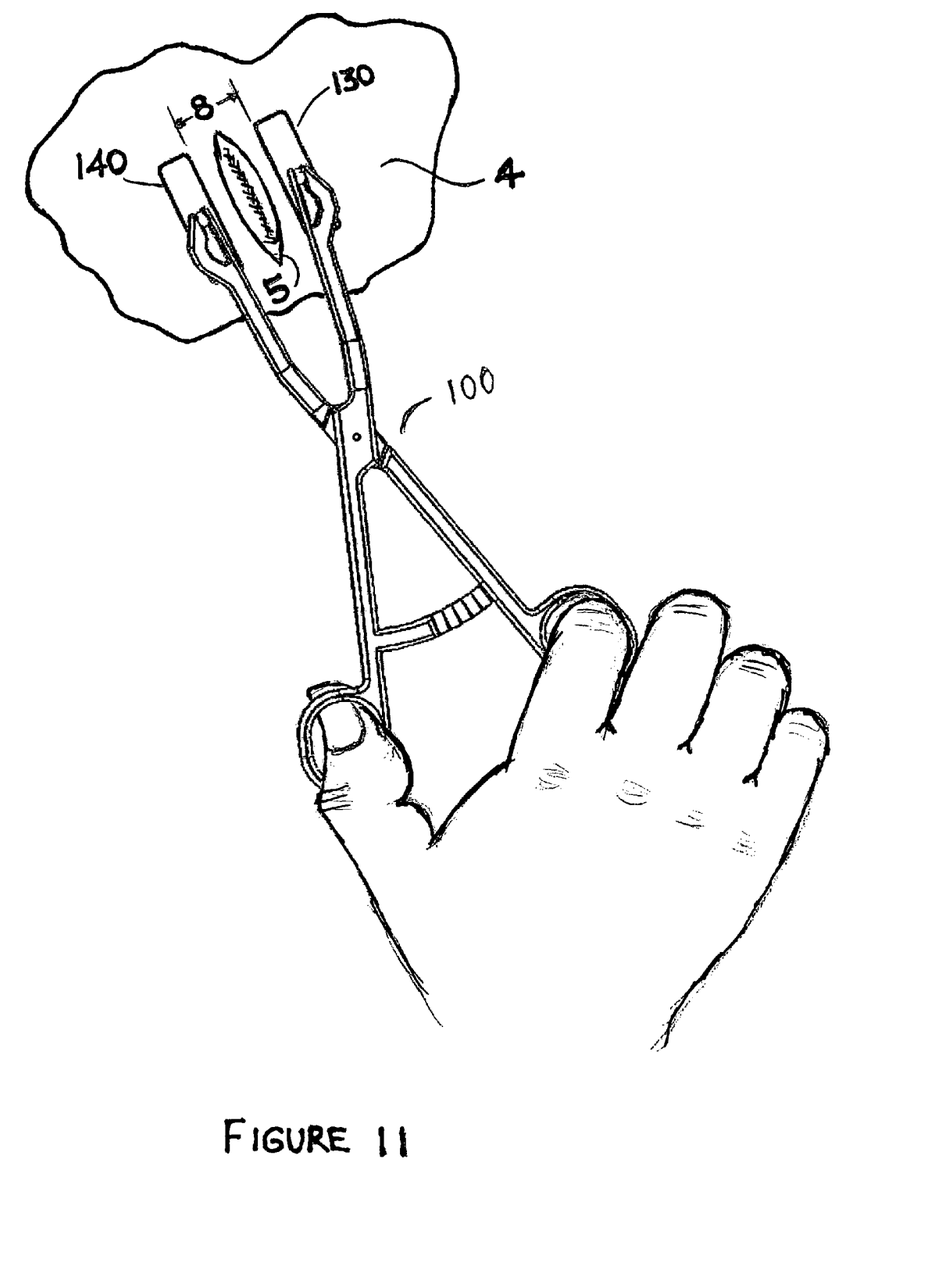
FIG. 11 depicts how the tissue approximation device would be utilized.

As an example, the tissue approximation device may be used in the following manner as depicted in FIG. 11. The release paper would be stripped off from the pressure sensitive adhesive pads 130, 140 to expose the adhering surface having the pressure sensitive adhesive. The adhesive pads 130, 140 may be either pre-assembled on the tongs 112b, 114b of the forceps 100 or attached to the tongs after the adhesive pads 130, 140 are positioned onto the skin tissue 4 on the opposed sides of a wound 5, i.e., straddling the wound. A light pressure would then be used to secure the adhesive pads 130, 140 to the skin tissue 4. The physician would then approximate the wound 5 by actuating the forceps 100 in a direction to move the adhesive pads 130, 140 towards each other in a common plane that is generally parallel to the skin tissue 4, and engaging the ratchet mechanism 124 to assure that the edges surfaces of the wound 5 do not move while the wound closure means is applied to the wound 5. Specifically, when the forceps 100 is in an actuated mode, the adhesive pads 130, 140 align to form a gap 8 between the adhesive pads 130, 140 to allow for the application of the wound closure means to the wound 5. With the tissue approximation device of the present invention, a wound may be approximated without substantially everting the edge surfaces of the wound, during application of the wound closure means. After the wound closure means has been applied, the tongs 112*b*, 114*b* may be removed from the adhesive pads 130, 140, if detachable, followed by removal of the adhesive pads 130, 140 from the skin tissue 4. Alternatively, adhesive pads 130, 140 may be removed from skin tissue 4 while still attached to tongs 122*b*, 114*b*. Adhesive pads 130, 140 are specifically designed to have high shear resistance to hold maintain approximation of the wound 5, but low peel resistance for easy removal from the skin tissue 4 once the wound closure means has been applied.

What is claimed is:

1. A tissue approximation device comprising two elongate arms having proximal and distal ends, an attachment means to secure the elongate arms to each other at one or more locations, adhesive pads movably connected on the ends of the elongate arms to anchor the tissue approximation device to the skin, and a locking means to lock the elongate arms in place relative to each other, wherein (i) the adhesive pads are spaced apart from the one or more locations of the attachment means in the direction of the elongate arms, and (ii) the tissue approximation device has an open position and a closed position, and when in the closed position, the adhesive pads are parallel and non-contiguous to each other, where the adhesive pad has a first adhering surface and a second surface rotatably coupled to the distal end of each of the elongate arms by a ball and socket connector, wherein the second surface has one of a socket and a ball that communicates with the other one of a ball and a socket on the distal end of each of the elongate arms, and the adhesive pad is rotatable around the ball and socket connector about at least two axes.

2. The tissue approximation device of claim 1, where the elongate arms form a pair of forceps, the attachment means is a yoke on the forceps, and the locking means is a ratchet mechanism on the forceps.

3. The tissue approximation device of claim 2, where the distance between the elongate arms is adjustable by means of a ratchet mechanism.

4. The device of claim 1, wherein the second surface has the socket and the distal end has the ball.

5. The device of claim 1, wherein the second surface has the ball and the distal end has the socket.

6. The device of claim 1, wherein the second surface and the distal end of the elongate arm connect in a snap fit manner.

7. A tissue approximation device for application to a skin surface adjacent to a wound, comprising:
   a pair of arms, each arm having a longitudinal axis and opposed ends, wherein one end includes a handle and the other end includes a tong with a connector;
   an attachment mechanism coupled to each arm that movably couples the arms to each other so that a distance between each tong is selectively variable;
   an adhesive pad removably coupled to the connector of each tong, wherein each adhesive pad has an adhesive surface that extends in a plane generally parallel to the longitudinal axis of the respective tong, the adhesive surface having a high shear resistance for holding the skin surface and a low peel resistance for removal from the skin surface, and wherein the connectors support the adhesive pads to be positionable in a common plane on opposed sides of the wound and conform to the skin surface adjacent to the wound; and
   a locking mechanism coupled to each arm to selectively lock the pair of arms in a fixed position relative to each other,
   wherein the coupling is rotatable and connects the adhesive pad to the tong so as to pivot at least about the longitudinal axis and an axis substantially perpendicular to the longitudinal axis and the connector is one of a ball and a socket and the adhesive pad includes the other of the ball and the socket, wherein the ball and socket are snap fit together in an interference fit.

8. The device of claim 7, wherein the arms are connected in a scissors configuration.

9. The device of claim 7, wherein the adhesive pad includes serrations that provide flexibility to the adhesive surface.

10. The device of claim 7, wherein the locking mechanism includes a ratchet.

11. The device of claim 7, wherein the arms are made of a resilient material.

* * * * *